(12) United States Patent
Richards

(10) Patent No.: US 7,282,603 B2
(45) Date of Patent: Oct. 16, 2007

(54) ANHYDROUS PROCESSING OF METHANE INTO METHANE-SULFONIC ACID, METHANOL, AND OTHER COMPOUNDS

(76) Inventor: Alan K. Richards, 994 Lighthouse Dr., Palm City, FL (US) 34990

( * ) Notice: Subject to any disclaimer, the term of this patent is extended or adjusted under 35 U.S.C. 154(b) by 33 days.

(21) Appl. No.: 10/873,361

(22) Filed: Jun. 21, 2004

(65) Prior Publication Data

US 2005/0070614 A1    Mar. 31, 2005

Related U.S. Application Data

(60) Provisional application No. 60/480,183, filed on Jun. 21, 2003.

(51) Int. Cl.
*C07C 309/00* (2006.01)
*C07C 41/00* (2006.01)

(52) U.S. Cl. ...................... 562/123; 568/698

(58) Field of Classification Search ............... 562/123; 568/698

See application file for complete search history.

(56) References Cited

U.S. PATENT DOCUMENTS

| | | |
|---|---|---|
| 2,492,984 A | 1/1950 | Grosse et al. |
| 2,493,038 A | 1/1950 | Snyder et al. |
| 2,553,576 A | 5/1951 | Grosse et al. |
| 3,927,189 A | 12/1975 | Jayawant |
| 3,969,427 A | 7/1976 | Bell et al. |
| 5,233,113 A | 8/1993 | Periana et al. |
| 5,306,855 A | 4/1994 | Periana et al. |
| 6,207,025 B1 | 3/2001 | Eiermann et al. |
| 6,380,444 B1 | 4/2002 | Bjerrum et al. |
| 6,384,271 B1 | 5/2002 | Jacobson et al. |
| 6,452,058 B1 | 9/2002 | Schweizer et al. |
| 6,495,714 B1 | 12/2002 | Halbritter et al. |
| 6,531,629 B1 | 3/2003 | Eiermann et al. |
| 6,538,162 B2 | 3/2003 | Chang et al. |
| 2002/0103402 A1 | 8/2002 | Chang et al. |

FOREIGN PATENT DOCUMENTS

| | | |
|---|---|---|
| DE | 10132526 | 1/2003 |
| GB | 632820 | 5/1947 |

OTHER PUBLICATIONS

Mukhopadyay et al., direct liquid phase sulfonation of methane to methanesulfonic acid by sulfur trioxide, (Angew. Chem. Int. Ed. 2003, 42, No. 9.*
Afrasiabi, K., "China rocks the geopolitical boat," Asia Times Online, Nov. 6, 2004.
Arndsten, M.G., et al "Selective Intermolecular Carbon-Hydrogen Bond Activation by Synthetic Metal Complexes in Homogeneous Slution," Acc. Chem. Res., 154-162 (1995).
Basickies, N, et al, "Radical-initiated functionalization of methane and ethane in fuming sulfuric acid," J Am Chem Soc 118: 13111-13112 (1996).
Eiermann, M., et al "The influence of the quality of methanesulphonic acid in electronic and electroplating applications," BASF Performance Chemicals Brochure (2002).
Gesser, H.D., et al, "The Direct Conversion of Methane to Methanol by Controlled Oxidation," Chem Rev 85: 235 (1985).
Gilbert, G.E., Sulfonation and Related Reactions (Interscience Publishers, pp. 1-9 (1965).
Golombok, M., et al, "A chemical alternative to natural gas flaring," Ind Eng Chem Res 42: 5003-5006 (2003).
Lin, M., et al, "Oxidation and oxidative carbonylation of methane and ethane by hexaono-u-peroxodisulfate(2-) ion in aqueous . . . " J Chem Soc Chem Comm 1992: 892-893 (1992).
Lin, M. et al, "Catalytic Carbon—Carbon and Carbon-Hydrogen Bond Cleavage in Lower Alkanes . . . " J. Am. Chem. Soc. 118: 4574 (1996).
Lobree, L.J., et al, "K2S2O2-initiated sulfonation of methane to methanesulfonic acid," Ind Eng Chem Res 40: 736-742 (2001).
Mukhopadhyay, S., et al, "Effects of solvent acidity on the free-radical-initiated synthesis of methanesulfonic acid from CH4 and SO3," Ind. Eng. Chem. Res. 41, 5901-05 (2002).
Mukhopadhyay, S., et al, "A novel method for the direct sulfonation of CH4 with SO3 in the presence of KO2 and a promoter," Organic Process Res & Dev 2003: A-D (2003).
Mukhopadhyay, S., et al, "A high-yield approach to the sulfonation of methane to methanesulfonic acid initiated by H2O2 and a metal . . . ," Angew Chem Int Ed 42: 2990-93 (2003).
Mukhopadhyay, S, et al., "Direct Sulfonation of Methane to Methanesulfonic Acid with SO2 Using Ca Salts as Promoters," J. Am. Chem. Soc., 4406-4407. (2003).
Mukhopadhyay, S., et al, "Synthesis of methanesulfonic acid and acetic acid by the direct Sulfonation of carboxylation of methane," Stud. Surf. Sci. Catal. 147: 523-528 (2004).
Mukhopadhyay, S et al., "Catalyzed Sulfonation of Methane to Methanesulfonic Acid," Journal of Molecular Catalysis A: Chemical, 211: 59-65 (2004).

(Continued)

*Primary Examiner*—J. Parsa
(74) *Attorney, Agent, or Firm*—Patrick D. Kelly

(57) ABSTRACT

Anhydrous processing to convert methane into oxygenates (such as methanol), liquid fuels, or olefins uses an initiator to create methyl radicals. These radicals combine with sulfur trioxide to form methyl-sulfonate radicals. These radicals attack fresh methane, forming stable methane-sulfonic acid (MSA) while creating new methyl radicals to sustain a chain reaction. This system avoids the use or creation of water, and liquid MSA is an amphoteric solvent that increasing the solubility and reactivity of methane and $SO_3$. MSA from this process can be sold or used as a valuable chemical with no mercaptan or halogen impurities, or it can be heated and cracked to release methanol (a clean fuel, gasoline additive, and chemical feedstock) and sulfur dioxide (which can be oxidized to $SO_3$ and recycled back into the reactor). MSA also can be converted into gasoline, olefins, or other valuable chemicals.

27 Claims, 6 Drawing Sheets

OTHER PUBLICATIONS

Mukhopadhyay, S., et al, "A High-Yield, Liquid-Phase Approach for the Partial Oxidation of Methane to Methanol using SO3 as the Oxidant," Adv. Synth. Catal. 347: 1203-6 (2005).

Nizova, G.V., et al, "Carboxylation of methane with CO or CO2 in aqueous solution catalysed by vanadium complexes," Chem Commun: 1885-1886 (1998).

Olah, G.A., et al, "Onium-based Chemistry: 1. Bifunctional Acid-Base-Catalyzed Conversionof Heterosubstitutes Methanes . . . ," J. Amer. Chem. Soc. 106: 2143-2149 (1984).

Olah, G.A., "Electrophilic Methane Conversion," Acc Chem Res 20: 422 (1987).

Pyatnitskii, Y.I., "Contemporary methods for the direct catalytic conversion of methane," Theor Exper Chem 39: 201-218 (2003).

Periana, R.A., et al, "A mercury-catalyzed, high-yield system for the oxidation of methane to methanol," Science 259: 340 (1993).

Periana, R.A., et al, "High yield conversion of methane to methyl bisulfate catalized by iodine cations," Chem Commun: 2376-2377 (2002).

Reis, P.M., et al, "Single-pot conversion of methane into acetic acid in the absence of CO and with vanadium catalysts such as amavadine," Angew Chem Int Ed 42: 821-823 (2003).

Seventh Natural Gas Conversion Symposium, Jun. 2004, Program, www.dicp.ac.cn/hezuo/huiyi/word/Binderok.pdf.

Te Velde, G., et al, "Chemistry with ADF [Amsterdam Density Functional software]," J Comput Chem 22: 931 (2001) (abstract).

Zerella, M., et al, "Synthesis of mixed acid anhydrides from methane and carbon dioxide in acid solvents," Amer Chem Society 5: 3193-3196 (2003).

Zhou, X., et al, "An integrated process for partial oxidation of alkanes," Chem. Commun. 2294-2295 (2003).

* cited by examiner

Formation of methyl radicals

Anhydrous radical-initiated system: $SO_3$ in, $SO_2$ out, converts methane to methanol Conversion of methane to liquid fuel, using MSA-to-methanol cracking step Conversion of methane to liquid fuel, using direct MSA on Zeolite

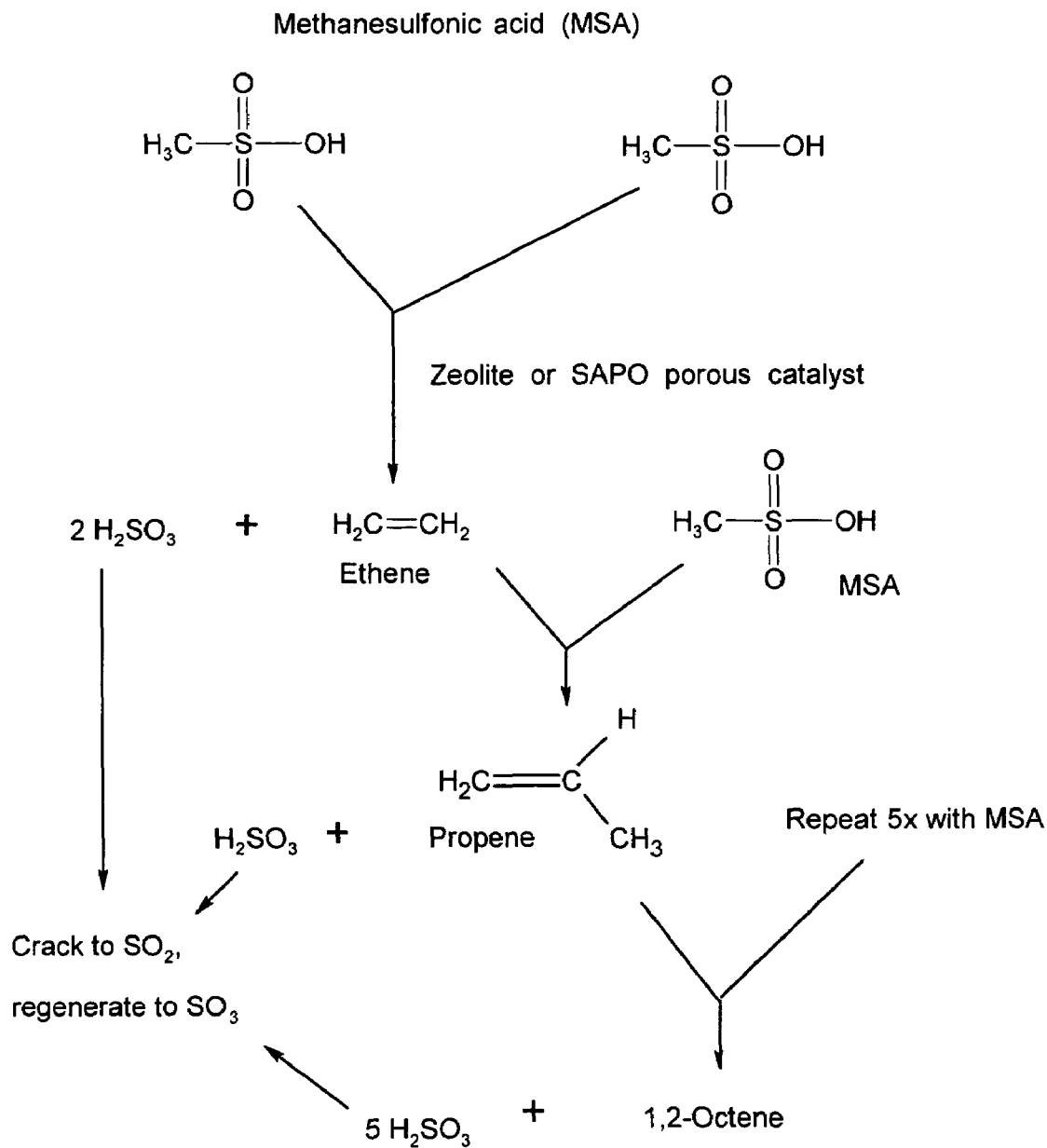
Fig. 6  Stepwise condensation of MSA to octene

ANHYDROUS PROCESSING OF METHANE INTO METHANE-SULFONIC ACID, METHANOL, AND OTHER COMPOUNDS

RELATED APPLICATION

This application claims priority under 35 USC 119(e) based on provisional application 60/480,183, filed on Jun. 21, 2003.

FIELD OF THE INVENTION

This invention relates to organic chemistry, hydrocarbon chemistry, and processing of methane gas.

BACKGROUND OF THE INVENTION

Because there have been no adequate chemical methods for converting methane gas into liquids that can be transported efficiently to commercial markets, very large quantities of methane gas are wasted every day, by flaring, reinjection, or other means, at fields that produce crude oil. In addition, numerous gas fields are simply shut in, at numerous locations around the world.

Skilled chemists have tried for at least 100 years to develop methods for converting methane gas into various types of liquids. While various efforts in the prior art could produce relatively small quantities and low yields of methanol or other liquids, none of those efforts ever created yields that were sufficient to support commercial use at oil-producing sites. Such efforts prior to 1990 are described in reviews such as Gesser et al 1985 and Olah 1987 (full citations to all articles and books are provided below), and efforts after 1990 are described in articles such as Periana et al 1993, 1998, and 2002, Basickes et al 1996, Lobree et al 2001, and Mukhopadhyay 2002 and 2003.

As a result, oil and chemical companies are investing (as of early 2004) huge amounts of money to design and build facilities that will use either "liquified natural gas" (LNG), or a processing system called "Fischer-Tropsch". However, both of those systems are very inefficient and wasteful.

LNG processing burns about 40% of a methane stream, to refrigerate the remainder to somewhere between −260 and −330° F., causing it to liquefy so it can be loaded into specialized ocean-going tankers. After a tanker reaches its destination, another large portion of the methane must be burned, to warm the methane back up to temperatures that allow it to be handled by normal pipes and pumps. Therefore, LNG wastes roughly half of a methane stream. Nevertheless, as of early 2004, oil companies had committed an estimated $30 billion to build LNG facilities.

Similarly, Fischer-Tropsch processing burns about 30% of a methane stream to convert the remainder into a mixture of carbon monoxide and hydrogen, called "synthetic gas" or "syngas". The syngas is then converted (using expensive catalysts) into heavy oils and paraffins, which then must be cracked and/or distilled to convert them into gasoline and other products. The syngas conversion, the catalyst costs, and the fact that the process makes thick and heavy oils and waxes that require still more processing, all create major inefficiencies, but as of early 2004, companies have committed to building Fischer-Tropsch facilities costing tens of billions of dollars.

The waste and inefficiencies of LNG and Fischer-Tropsch systems, which are receiving billions of dollars in investments, prove the assertion that any methane-to-methanol systems previously proposed, based on small-scale laboratory work, have not been regarded as commercially practical, by any major companies. In addition, it should be noted that most processing systems proposed to date generate large quantities of acidic and hazardous byproducts and toxic wastes. Even if they can be recycled, those byproducts and wastes poses major obstacles to efficient and economic use.

Additional background information is provided in Patent Cooperation Treaty application number WO 2004/041399, arising from application PCT/US03/035396, filed in November 2003 by the same Applicant and Inventor herein. The contents of that published application are incorporated herein by reference.

PRIOR ART METHODS FOR MAKING MSA

Because of its role in processes described herein, attention must be given to a compound called methanesulfonic acid, abbreviated as MSA and having the formula $H_3C-SO_3H$. MSA has been known for many decades, and is sold as a commodity chemical, mainly for use in processes such as metal cleaning, electroplating, and semiconductor manufacturing.

One set of prior art that relates to MSA is contained in several patents issued to John Snyder and Aristid Grosse, based on work they did for the Houdry Process Company in the 1940's. Those patents include U.S. Pat. No. 2,492,983 ("Methanol Production"), U.S. Pat. No. 2,493,038 ("Reaction of Methane with Sulfur Trioxide"), U.S. Pat. No. 2,553,576 ("Production of Organic Compounds from Methane Sulfonic Acid"), and U.S. Pat. No. 2,492,984 ("Organic Reactions", focused largely on the formation of liquid hydrocarbons from methanol). Although their chemical insights were groundbreaking, and provided key insights and building blocks that were used by the Applicant herein, the work by Snyder and Grosse in the 1940's never led to good yields of desired products, and never led to commercial use of those processes. In addition, much of their work used catalysts such as mercury, which is highly toxic. Accordingly, their methods of making MSA are not in use today, and other methods have been developed.

Briefly, there are three main methods that have been used commercially in the prior art, for manufacturing MSA. All three methods are described and compared in a technical sales brochure published by the BASF company (Ludwigshafen, Germany), by M. Eiermann et al, entitled, "The influence of the quality of methanesulphonic acid in electronic and electroplating applications" (2002, BASF brochure E-EVD/GK-I 550). That brochure describes various advantages of the BASF method over the two other prior commercial methods of manufacture.

One prior art method uses chloroxidation of methylmercaptan, to form MSA chloride, which is then hydrolyzed to release MSA. The two main reactions are:

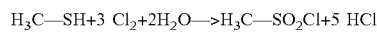

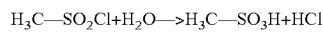

The disadvantages of that system, according to BASF, included: (1) the raw materials are toxic and expensive; (2) large amounts of hydrochloric acid wastes are formed; and, (3) the MSA product must be purified by extraction and stripping.

The second prior art method is called "the salt process", and uses the following reaction:

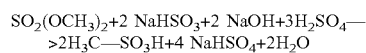

The disadvantages of that system, according to BASF, included: (1) large amounts of salt wastes are formed; (2) solids must be removed from the system; and (3) it must be carried out using batch processing, rather than in a continuous-flow steady-state reaction.

The BASF system uses a two-step reaction, starting with methanol, elemental sulfur, and hydrogen, to get dimethyldisulfide, which is then catalytically oxidized into MSA, as follows:

$$2H_3COH + H_2 + 2S \rightarrow H_3C-S-S-CH_3 + 2H_2O$$

$$H_3C-S-S-CH_3 + 5/2O_2 + H_2O \rightarrow 2H_3C-SO_3H$$

Although that system does indeed offer a number of advantages over the two other systems, it should be noted that pure methanol, pure hydrogen gas, and pure elemental sulfur are all comparatively expensive, compared to the reagents used in the process disclosed herein. In addition, the BASF brochure indicates that its MSA product contains 7 parts per million (ppm) sulfate impurities, and 1 to 2 ppm chloride impurities. Their MSA product also requires distillation, to separate it from at least nine identified possible impurities, including $H_3CS(O)CH_3$, $H_3CS(O_2)CH_3$, $H_3CS(O_2)SCH_3$, $H_3CS(O_2)OCH_3$, $H_3CS(O_2)S(O)CH_3$, and sulfuric acid; and, because of chemical similarities, various of those impurities may be present, at low but potentially significant quantities, in the final distilled product.

The process disclosed herein for making MSA is believed to provide an improved method of manufacture which appears capable of creating preparations of MSA that contain no residual "mercaptan" compounds (having the general formula R—SH), and no residual halogen atoms, such as chloride or fluoride atoms. Since mercaptan or halogen impurities can create substantial problems when MSA is used for high-tech manufacturing purposes (especially in making semiconductor materials), the absence of mercaptan or halogen impurities, in MSA made by the methods herein, appears to offer an important and valuable advance in the art.

In addition, this new method of manufacture begins with methane, rather than methanol. Since methanol does not occur naturally in any substantial quantities, it must be manufactured somehow, to make MSA via the BASF process, and the total transportation costs are likely to be considerable (for example the largest BASF plant used to make MSA is in Germany, and Germany has no natural supplies of methane or crude oil). By contrast, methane gas is available in huge quantities around the world, and roughly $100 million worth of methane is flared or reinjected, every day, as an unwanted, explosive, and dangerous byproduct of crude oil production, at thousands of sites where it is not feasible or economical to transport the methane to distant markets.

It must be recognized that the world market for MSA is only a tiny fraction of the world market for methanol (which can be used as a clean-burning liquid fuel, as a gasoline additive, as a chemical feedstock, and for various other uses). Therefore, the main utility and value of this invention, which produces high-purity MSA, will come from either: (1) "cracking" the MSA, to release methanol (which has unlimited markets) and sulfur dioxide (which can be regenerated into $SO_3$ and recycled back into the reactor that converts methane into MSA), or (2) processing the MSA in other ways, such as by passing it through porous catalysts such as Zeolite or "SAPO", to convert it into liquid fuels, olefins, or other compounds, as described below.

Nevertheless, it should be noted that the process disclosed herein can be used to make hugh-purity, high-quality MSA, as a commodity chemical that can be sold and used directly for electroplating, semiconductor manufacturing, or other industrial or commercial purposes.

Therefore, one object of this invention is to disclose a system for converting methane into high-quality MSA that contains no mercaptan or halogen impurities.

Another object of this invention is to disclose a system for converting methane into methanol, via a pathway that uses MSA as an intermediate, in a more efficient and selective and less expensive manner than any prior known system, with thermodynamic barriers that are lower than ever previously known.

Another object is to disclose a system that converts methane into MSA or methanol, while creating only very small quantities of waste or byproducts, by using a combination of (i) radical-initiated chain reactions that lead from methane to MSA, and (ii) recycling methods that recover and reuse any inorganic reagents, catalysts, or intermediates.

These and other objects of the invention will become more apparent through the following summary, description, and figures.

SUMMARY OF THE INVENTION

Reagents and methods that utilize radicals (highly reactive atoms or molecules with an unpaired electron) are disclosed, for converting small hydrocarbons such as methane into oxygenated compounds, such as methanol. The reaction system uses any of several known pathways to efficiently remove a hydrogen atom (both a proton and an electron) from methane ($CH_4$), generating methyl radicals ($H_3C^*$). The methyl radicals combine with sulfur trioxide ($SO_3$), to form methyl-sulfonate radicals. The methyl-sulfonate radicals attack methane that is being added to the reactor, and remove hydrogen atoms. This forms stable methane-sulfonic acid (MSA, $H_3C-SO_3H$), and also creates new methyl radicals, which can sustain a chain reaction while methane and $SO_3$ are continuously added to the reactor vessel. This system uses anhydrous conditions to avoid the use or creation of water or other unnecessary molecules, and liquid MSA also functions as an amphoteric solvent, which increases the solubility and reaction rates of the methane and $SO_3$.

MSA that is removed from the reactor can be used in any of several ways. It can be sold as a valuable chemical that will not contain mercaptan or halogen impurities. Alternately, it can be heated to release methanol (which has unlimited markets as a clean fuel, gasoline additive, and chemical feedstock) and sulfur dioxide (which can be oxidized to $SO_3$ and recycled back into the reactor). Alternately, MSA can be converted into gasoline or other hydrocarbon liquids (using Zeolite catalysts), olefins (using SAPO catalysts), or other valuable chemicals.

BRIEF DESCRIPTION OF THE DRAWINGS

FIG. 6 depicts condensation of 1,2-octene, with molecules of MSA inserting methylene (—$CH_2$—) groups into the double bond of a growing olefin chain.

DETAILED DESCRIPTION

As briefly summarized above, anhydrous pathways that use radicals (atoms or molecules with an unpaired electron) are disclosed for converting small hydrocarbons (such as methane) into oxygenated or other intermediates or products (such as methane-sulfonic acid, which can be heated to release methanol).

Figure 1:
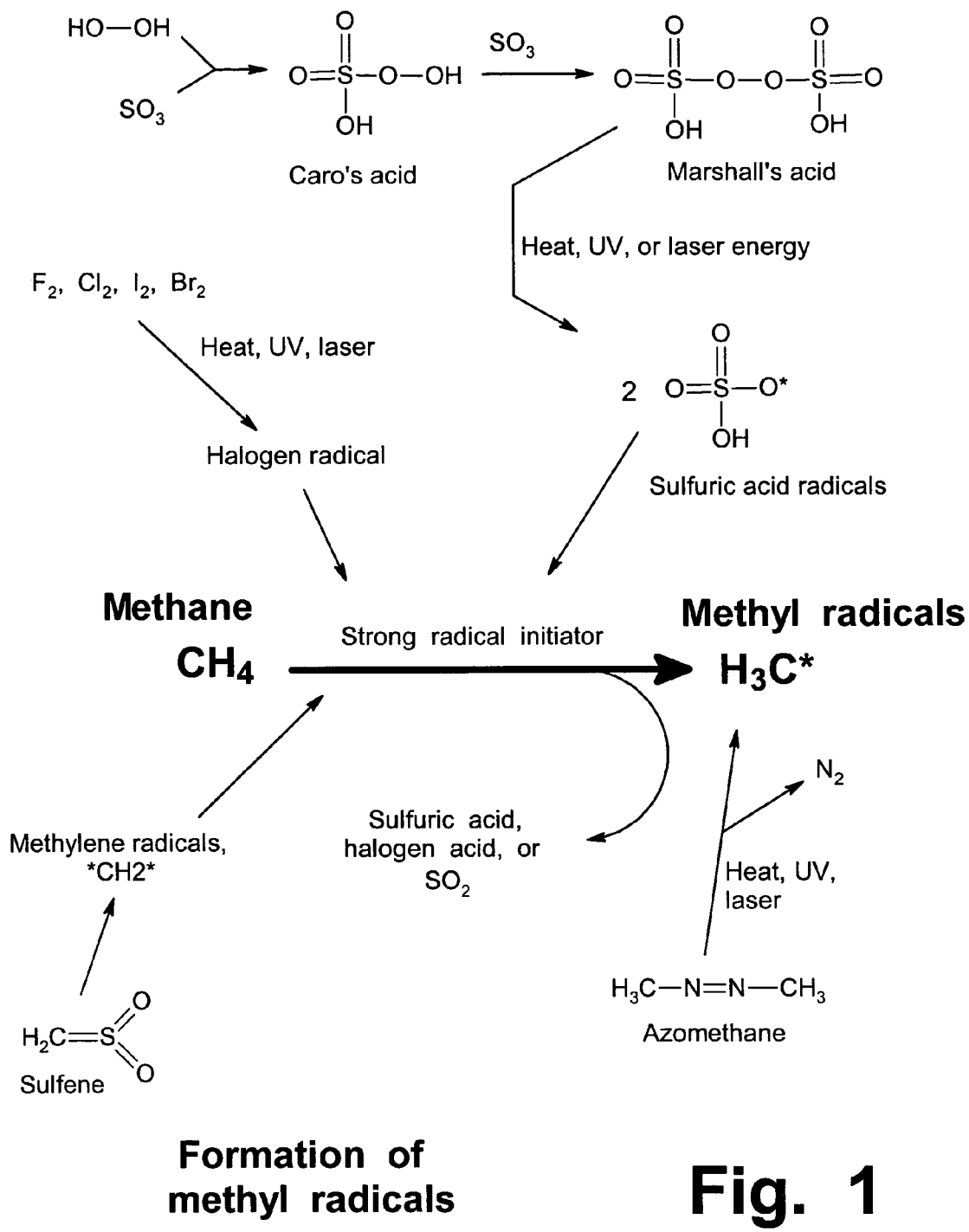
FIG. 1 depicts several known chemical reactions that can "activate" methane ($CH_4$) by removing a hydrogen atom (both a proton and an electron), to convert the methane into a methyl radical ($H_3C^*$, where the asterisk represents an unpaired electron).

As depicted in FIG. 1, several methods are known for creating methyl radicals ($H_3C^*$, with the asterisk depicting an unpaired electron). The chemical methods require radical initiators that are substantially stronger than hydroxy radicals of the type that are released by hydrogen peroxide, HOOH. One method involves manufacturing a compound called Marshall's acid, the common name for peroxy-disulfuric acid, which has the formula $HO_3SO—OSO_3H$. This compound can be synthesized by methods such as: (1) reacting hydrogen peroxide with $SO_3$ to form peroxy-monosulfuric acid, $HO_3SOOH$, which has the common name Caro's acid, and (2) adding more sulfur trioxide to the Caro's acid, to convert it to Marshall's acid. More information on methods, equipment, and reaction conditions for making Marshall's acid is provided in U.S. Pat. No. 3,927,189 (Jayawant 1975).

When Marshall's acid is treated by a suitable energy input (such as mild heating, ultraviolet (UV) light, or a laser beam with a "tuned" wavelength), in the presence of a catalyst if desired (such as solid catalytic surfaces as described in articles such as Lie et al 2002, and in other works cited in footnotes 22-52 in Lie et al 2002), the peroxide bond will break, releasing two identical radicals with the formula $HO_3SO^*$. These can be regarded either as Marshall's acid radicals (since they came from Marshall's acid), or as sulfuric acid radicals (since they are sulfuric acid that is missing a hydrogen atom). These radicals are much stronger than conventional hydroxy radicals ($HO^*$), and unlike hydroxy radicals, they can efficiently remove hydrogen atoms from methane, to convert the methane into methyl radicals, while also creating stabilized sulfuric acid. Because a small quantity of Marshall's acid will trigger a chain reaction that will keep going and convert a large quantity of methane into MSA and/or methanol, the amount of sulfuric acid waste will be small, if Marshall's acid is used as the radical initiator.

Other methods for creating methyl radicals are known, and include the following, as examples:

(1) using other known chemicals that contain sulfur, phosphorous, or nitrogen structures that can be activated by an energy source such as heating, UV radiation, or a tuned laser beam, to release "strong radicals" that are strong enough to efficiently remove hydrogen atoms from methane; or, (2) using heat, UV, laser, or other energy input to break apart a halogen gas (such as fluorine or chlorine gas, $F_2$ or $Cl_2$, etc.) into radicals that will remove hydrogen atoms from methane;

Various types of energy-transfer devices can be used to break apart susceptible chemicals into radicals. One class of devices can be referred to as "radical guns" or "radical pumps", since these devices can shoot or pump radicals out of a nozzle that contains very hot heating elements (such as white-hot electrical filaments inside protective sleeves made of quartz or similar materials that will conduct heat but not electricity). These devices can inject radicals directly into a stream of methane and/or sulfur trioxide, minimizing any chances for the radicals to react in undesired ways. Radical guns with heating elements are described in articles such as Danon et al 1987, Peng et al 1992, Chuang et al 1999, Romm et al 2001, Schwarz-Selinger et al 2001, Blavins et al 2001, and Zhai et al 2004. Similar devices can be developed with nozzles that use ultraviolet or laser radiation (in combination with catalytic surfaces, if desired) to break apart molecules passing through the nozzle, in ways that form radicals that can efficiently remove hydrogen from methane.

Any such devices can be evaluated for use as disclosed herein, with any candidate radical initiator compound. One such compound is azomethane, $H_3C—N=N—CH_3$. If energized in a suitable manner, azomethane will release methyl radicals, along with nitrogen gas, $N_2$, which is relatively inert, nontoxic, and present in large quantities in the atmosphere. Other candidate radical initiators include anhydrides of MSA, which include sulfene, $H_2C=SO_2$, an "inner anhydride" formed by removing water from a single molecule of MSA), and an "outer anhydride" formed by combining two molecules of MSA while removing a molecule of water.

Accordingly, various methods for creating methyl radicals are known, and are generally represented by FIG. 1.

Figure 2:
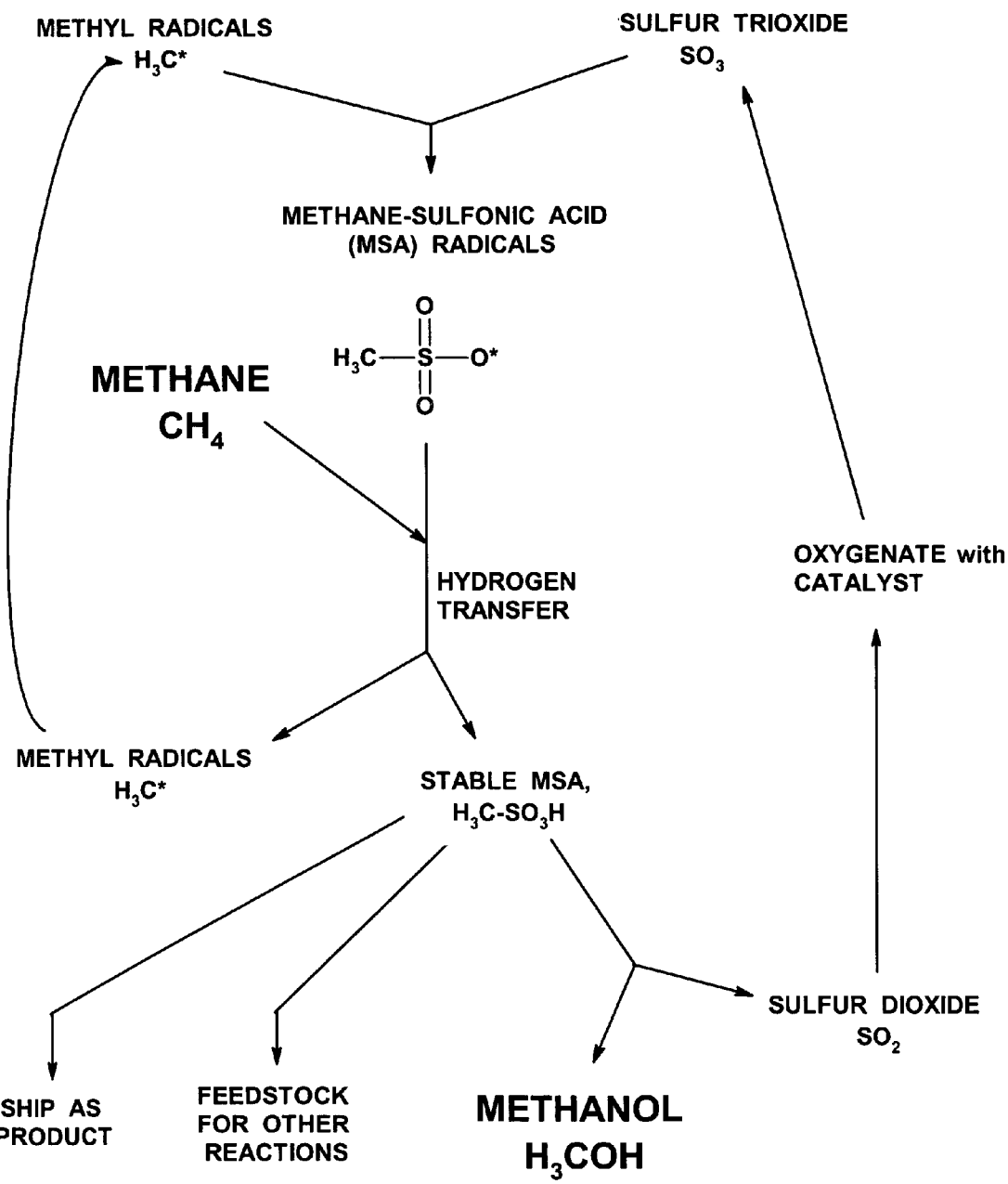
FIG. 2 depicts a reaction system that combines methyl radicals ($H_3C^*$) and sulfur trioxide, to form methane-sulfonic acid (MSA) by a multi-step process that creates a new methyl radical. This establishes a chain reaction, and the newly-created methyl radicals will react with newly-added $SO_3$. MSA can be removed from the vessel and sold as a product, used as a reagent, or "cracked" to release methanol (which can be shipped as a liquid, or used as a feedstock for other reactions) and sulfur dioxide (which can be oxidized to $SO_3$ and recycled back into the reactor).

The methyl radicals are used, inside a continuous flow reactor vessel (described below) to initiate a chain reaction that will convert methane gas into methane-sulfonic acid (MSA), as shown in FIG. 2. As illustrated, the methyl radicals bond to sulfur trioxide, to form methane-sulfonic acid (MSA) radicals (possibly mixed with some quantity of isomers or other species, such as methyl bisulfite radicals, as discussed below). These radicals then remove hydrogen atoms from fresh methane that is being pumped into the reactor. This forms complete and stable MSA, which is a liquid that can be removed from the reactor by various means. It also creates a new supply of methyl radicals, which will keep the chain reaction going so long as methane and sulfur trioxide are added to the reactor at appropriate rates.

Certain types of computer modeling have raised a question as to whether methyl bisulfite ($H_3C—O—SO_2H$, an isomer of MSA with an oxygen between the carbon and sulfur) will also be formed. Tests carried out to date, using small closed batch reactors (such as described in the Examples below) have indicated that the bisulfite isomer does not occur in substantial quantities, and the MSA comprises at least about 99% of the organic portion of the liquid that is formed. Nevertheless, the possibility of forming bisulfites or other isomers or variants must be kept in mind as the process disclosed herein is tested and scaled up for continuous-flow reactors. It should also be noted that if methyl bisulfite is heated to a thermal cracking temperature, it will release methanol and $SO_2$, the same products released by MSA. Therefore, methyl bisulfite, if present, should not severely hinder the production of methanol from methane, but any intended products other than methanol will need careful evaluation, if an MSA mixture will be processed into such other products.

It should also be noted that various alternative compounds that may behave in similar ways can also be evaluated, for possible use as disclosed herein. For examples, other lower alkanes (such as ethane, propane, etc.) can be tested in place of methane, and various selected inorganic oxide compounds (such as various oxides of nitrogen or phosphorus, for example) can be tested in place of sulfur trioxide. Accordingly, methane and other compounds that will react and perform as disclosed herein are referred to, in some claims below, as alkane or lower alkyl compounds, sulfur trioxide and other compounds that will react and perform as disclosed herein are referred to, in some claims below, by terms such as "a selected inorganic alkylatable compound". Similar, methanol and other products thay can be created by such processing are referred to in some claims by terms such as "heavier" methylated or alkylated compounds.

MSA is both a product of the reaction shown in FIG. 2, and a solvent that helps keep that system running. It is an "amphoteric" solvent, since each molecule of MSA has two different domains. The methyl domain will help methane gas become dissolved in the liquid mixture (this process of dissolving methane in a liquid mixture can be accelerated by other means as well, such as (1) using emulsion reactors that generate high "shearing" forces to create foam-type emulsions, as described below, and possibly (2) using supercritical carbon dioxide, in liquid form). The sulfonic acid domain of MSA will help $SO_3$ mix rapidly with the liquid in the reactor.

Fresh methane and $SO_3$ will be continuously pumped into the reactor, and MSA will be continuously removed from the outlet. MSA has a number of manufacturing uses, and it can be sold, if desired, but the markets for MSA are small and limited, and the costs of tranporting hundreds or thousands of tons of $SO_3$ in an acid liquid are considerable. Since the MSA reactor will need a constant supply of $SO_3$ to keep running, a preferred use for MSA, in most cases, will involve either of two pathways.

In one pathway, the MSA can be heated to about 250 to 350° C., causing it to break apart, in a reaction called "thermolysis" or "cracking". This will split MSA into methanol and sulfur dioxide:

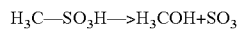

The methanol can be transported as a liquid through pipelines, tankers, etc. It has unlimited markets as a clean fuel, gasoline additive, or chemical feedstock. The $SO_2$ is oxidized back to $SO_3$, which is recycled back into the reactor, to reduce costs and avoid waste. This keeps the sulfur cycling through the reactor, entering as $SO_3$, and emerging as $SO_2$.

Various methods can be used to oxidize $SO_2$ to $SO_3$. At the current time, the most widely used commercial method uses vanadium pentaoxide ($V_2O_5$) as a catalyst, and recent improvement is disclosed in U.S. Pat. No. 6,572,835 (MacArthur et al, assigned to Chemithon). However, the Applicant herein is currently working on what appears likely to offer an improved system. Although that aspect of this disclosure is regarded as a separate invention, in a separate field of chemistry (which is being described in more detail in a separate and simultaneously-filed provisional application), it is also summarized herein, to ensure that the "disclosure of the best mode" requirement of the patent law is met.

Briefly, the reactor system, as currently contemplated by the Applicant herein, may be able to use porous "monolith" materials (which have essentially linear and parallel flow channels, as developed by various researchers, notably including Lanny Schmidt at the University of Minnesota), having an improved catalyst that is coated onto the interior surfaces of the flow channels that pass through the porous monolith. One promising catalyst that has been identified, through computer modeling, is vanadium perfluoro-diformate. Other candidate catalysts that will be evaluated include per-bromo, per-chloro, and per-iodo analogs, as well as other candidate catalysts that take vanadium to a +4, +5, or potentially +6 state. This may include compounds that replace the formate carbon atoms of the diformate compounds with other electronegative atoms, such as nitrogen, sulfur, or phosphorus, and compounds that contain a peroxide bridge between two adjacent vanadium atoms. Since formic acid derivatives with halogen atoms can be relatively unstable, chemists who are interested in such catalysts should evaluate articles such as Gilson 1994, and Li et al 1997, which describe methods for coating various fluorine-containing materials onto solid supports.

The conversion of $SO_2$ to $SO_3$ is an oxidation reaction that is highly exothermic, and it releases large quantities of heat. To remove excess heat from the $SO_3$ regenerator, and to make proper and efficient use of that energy, the tubing that contains the monolith reactor material preferably should be surrounded by an annular shell, which will function as a heat exchanger. This annulus will carry liquid MSA from the MSA reactor vessel, to a cracking (thermolysis) reactor. The MSA will enter the annular heat exchanger at a temperature that is likely to be in the range of about 70° C. or less, and it will need to be heated up to greater than 300° C. for thermolytic cracking, to release methanol and sulfur dioxide. Accordingly, a preferred system design should transfer the exothermic heat that is released by the $SO_2$ to $SO_3$ conversion, directly into MSA that needs to be heated up in order to crack it and release methanol.

More information on catalytic monolith materials can be obtained from sources such as U.S. Pat. No. 5,993,192 (Schmidt et al 1999), articles such as Raja et al 2000, and books such as Hayes et al 1997. Items that played key roles in establishing a foundation that supported the Applicant's analysis and development of improved vanadium catalysts were (1) FIG. 11, on page 114 of Dunn et al 1998, and (2) FIG. 4, and especially FIG. 4a, on page 214 of Giakoumelou et al 209. However, it must be emphasized that extensive and detailed study and analysis of numerous other published articles was also required, to enable the Applicant to move from certain starting points that were gleaned from those cited articles, toward the practical development of better catalytic materials and devices.

It must also be kept in mind that MSA can be processed directly into liquid hydrocarbons (such as gasoline), olefins, or other products or intermediates. Those pathways are described below.

Several factors should be noted about this method for converting methane into MSA, as illustrated in FIG. 2:

1. The pathway is anhydrous, and avoids or at least minimizes any presence, creation, or use of water (some small quantity of water may become present, if sulfuric acid or certain other sulfur species are created, and if some portion of those sulfur species breaks apart, such as into $H_2O$ and $SO_3$). It also avoids using metal or other salts. This anhydrous, non-salt approach makes the system more efficient, less corrosive, and less subject to fouling by mineral deposits inside vessels and pipes. It also reduces formation of byproducts and waste.

2. Because the pathways use radicals that are highly reactive, they have low thermodynamic barriers, and can run at relatively low temperature and pressure combinations, which can provide high efficiency, selectivity, and yields if the number of candidate reactants in the vessel are kept to a minimum.

3. By using chain reactions, these pathways generate large quantities of product with only small quantities of initiators and waste.

4. These pathways allow endless recycling of all sulfur compounds used or produced by the system. Even if MSA is directly converted into liquids or other compounds without passing through methanol, most such products do not contain sulfur, and the sulfur from MSA will be released by the processing system in ways that allow it to be recovered and reused.

5. Because of certain types of electron behavior, a methyl radical ($H_3C^*$) that is missing a hydrogen atom will not readily give up a second hydrogen atom. This is unlike various other reactions involving methane. For example, if methane is treated with a halogen such as chlorine, displacement of a first hydrogen atom can enable or even accelerate the loss of additional hydrogen atoms, leading to mixtures of carbon chlorides with one, two, three, or four chlorine atoms, which must then be separated if a single purified product is desired. However, the opposite happens when methane loses a hydrogen atom and becomes a radical.

These advantages are valuable, and can help enable high-yield processing and manufacturing operations with minimal hazards and wastes.

Furthermore, as mentioned in the Background section, it is believed that the reaction pathway disclosed herein can be designed and run in ways that completely avoid any use, presence, or formation of halogen or mercaptan compounds. Therefore, this method is believed to provide ways for manufacturing relatively pure preparations of MSA, which are characterized by the absence of any halogen or mercaptan compounds. Since the prior known methods for manufacturing MSA all suffered from some halogen or mercaptan impurities, this is believed to be a highly useful aspect of this invention. Accordingly, this application discloses and claims compositions of matter, comprising purified MSA preparations that are characterized by the absence of any halogen or mercaptan impurities.

It should also be noted that MSA, if made available in pure form and large quantities at sites that are widely distributed around the world, is likely to find a number of new and additional uses, as a research or manufacturing reagent or solvent. Because of the commercial importance of the system disclosed herein, the behavior and properties of MSA, as an amphoteric solvent, are likely to receive more careful attention and analysis, by chemists who previously have not previously paid any serious attention to MSA as a candidate solvent or reagent. After studying this system for more than a year, the Applicant has become convinced that MSA can play important roles in making better and more efficient use of numerous types of organic compounds, beyond those disclosed herein. Accordingly, the disclosure herein of an efficient and inexpensive way to manufacture large quantities of MSA, in relatively pure form that does not contain mercaptan or halogen impurities, is likely to promote the development of additional uses for MSA, beyond the uses and modes described herein.

Manufacturing System (Plant Layout)

Figure 3:
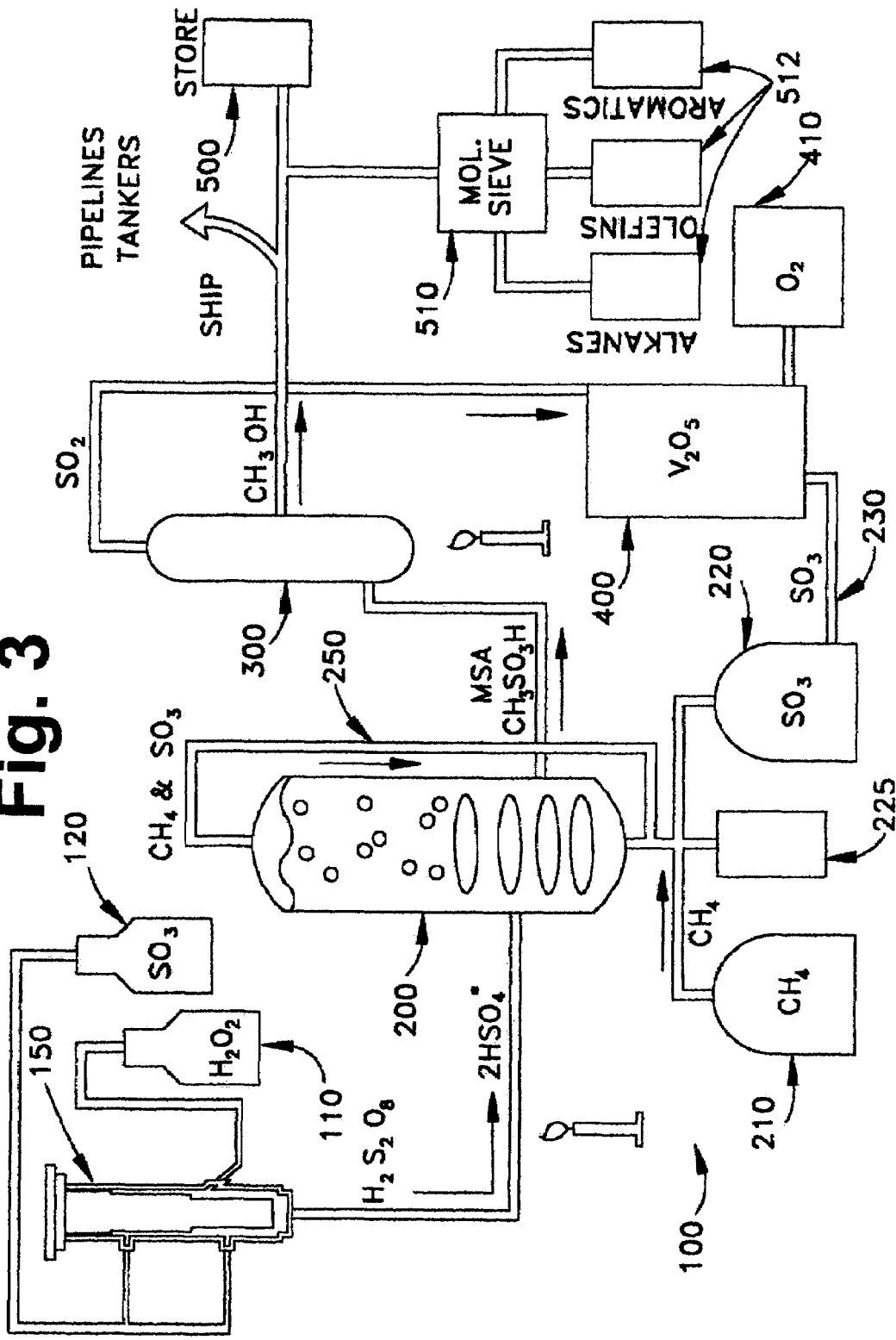
FIG. 3 depicts a methanol plant that uses Marshall's acid (with two sulfuric acid groups linked by a peroxide bond) to generate sulfuric acid radicals, which will efficiently remove hydrogen atoms from methane to create methyl radicals.

FIG. 3 provides a schematic layout of a manufacturing system 100 (often called a "plant" in the petrochemical industry) that can be used to carry out the reactions of this invention, if the Marshall's acid pathway is used. This illustration depicts the essential components of a simple and basic layout for creating methanol. This basic layout can be expanded, enhanced, and improved, in ways that will become apparent to those who design and build such facilities, depending on factors such as whether additional facilities for more complex processing of the MSA will be provided at this same facility. If other types of radical sources or initiators (other than the Marshall's acid system) are used, the only modifications that will be required in the illustrated plant layout, to handle that particular aspect of the overall process, will involve the devices in the upper left corner of FIG. 3, while the other components can remain essentially the same.

In a system that uses Marshall's acid, reagent supply container 110 contains hydrogen peroxide, $H_2O_2$. Reagent supply container 120 contains stabilized anhydrous liquid $SO_3$, or an alternate sulfonating agent that can be converted into Caro's acid and/or Marshall's acid. Both of these reagents are pumped into a suitable acid formation vessel 150, where they will combine and react to initially form Caro's acid (peroxy-mono-sulfuric acid, $HO_3SO$—$OH$). Additional $SO_3$ is then added at a subsequent inlet, and the Caro's acid is converted into Marshall's acid (peroxy-di-sulfuric acid, $HO_3SO$—$OSO_3H$). Acid formation vessel 150 is modelled after a similar vessel having annular reaction zones, shown in U.S. Pat. No. 5,304,360 for creating Caro's acid, modified by an additional inlet for $SO_3$ to convert the Caro's acid to Marshall's acid.

Marshall's acid will emerge from the bottom of acid formation vessel 150, and it will be heated, subjected to UV or laser radiation, or otherwise treated, to split it into $HSO_4^*$ radicals, as shown in FIG. 1. These radicals will be pumped, presumably in the form of a fine mist, entrained liquid, etc., into a main reactor vessel 200, which preferably should contain internal baffles, agitators, and/or other structures that will promote high levels of liquid/gas contact and interaction.

Main reactor vessel 200 will be receiving a steady supply of both methane and $SO_3$, from supply tanks 210 and 220 (via pump 225), and also from one or more recycling conduits 250 that will collect any unreacted methane or $SO_3$ that emerge from reactor 200. In most facilities that will deal with large volumes of methane that has been separated from crude oil at an oil field, methane supply tank 210 presumably will receive its supply of methane gas from a storage or surge tank that receives and holds pressurized methane gas, after the gas has been removed from crude oil in a separation vessel.

In cases in which sulfonated products are not removed and sold, the $SO_3$ supply will be continuously recycled; therefore, the "makeup" volumes that will be required to replace small and gradual losses will not be nearly as large as the volumes of methane that will be processed.

However, as noted above, MSA is a valuable chemical in its own right; indeed; it is worth roughly 10 times more than methanol, on an equal-weight basis. Therefore, it can be sold as a product, or used as a chemical feedstock, by sending some or all of the MSA that leaves the main reactor vessel 200 to a storage tank, rather than to a heating and cracking vessel 300 that will break the MSA into methanol and $SO_2$. If MSA or any other sulfonated product is removed from the system, the supplies of $SO_3$ that must be added will need to be increased, in a corresponding manner.

Any known method or machine for increasing the contact and interactions between the reagents inside the main reactor vessel 200 can be evaluated, using routine experiments, to determine their suitability for use as disclosed herein. For example, methane and $SO_3$ from supply pumps 210 and 220 might be pre-mixed, before they enter reactor vessel 200; alternately, they might be introduced in a counterflow manner, by introducing gaseous methane into the bottom of vessel 200, so that it will bubble and rise upward, while liquid $SO_3$ is pumped into the top of vessel 200 so that it will flow downward due to gravity. Similarly, any known or hereafter-discovered system, type, or combination of baffles, trays, meshes, fluidized particulate bed reactors, rotating or centrifugal reactors, loop reactors, oscillatory flow baffle reactors, high-shear reactors, $SO_3$-coated particulates, and other devices, methods, or formulations can be evaluated for use as disclosed herein, to determine whether they can improve the yields of the reactions disclosed herein.

In particular, three classes of candidate reactor vessels deserve mention, since any of them may be well-suited to carrying out various particular reactions. One class can be referred to as rotating, spinning, or centrifugal bed reactors. These are described in U.S. Pat. No. 4,283,255 (Ramshaw et al 1981, assigned to Imperial Chemicals), and U.S. Pat. No. 6,048,513 (Quarderer et al 2000, assigned to Dow Chemical Company). These devices normally use a fairly wide and thick disk that spins at high speed, to generate centrifugal force that will drive gases and liquids from one or more inputs near the center axle, toward the outside of the bed. They often use porous metallic mesh as the media, with supporting wires made of stainless steel or other relatively strong but inexpensive material, coated with a thin layer of an expensive catalyst, such as a soft or noble metal.

Another class of candidate reactor vessels that merit attention are often called "loop" reactors, or Buss (pronounced "boose") reactors, as described in U.S. Pat. No. 5,159,092 (Leuteritz 1992, assigned to Buss AG of Switzerland). This includes a subcategory called "monolithic" loop reactors, as described in Broekhuis et al 2001. Loop reactors typically use a combination of (1) a main reactor vessel, which contains a catalyst bed or other component that cannot be removed from the main vessel, and (2) a separate and usually smaller "secondary" vessel, which receives a liquid or gas stream that has been removed from the main vessel. The secondary vessel treats the portion of the liquid or gas stream which passes through it, and then returns it to the main reactor vessel. This allows the secondary vessel to help control and regulate what passes through the main vessel, without disrupting a catalyst bed or other system or device that operates inside the main vessel. As mentioned above, monolithic materials contain tiny but essentially parallel flow channels, to promote intimate contact between a liquid or gas and the solid surfaces of the material, without creating extremely high pressure drops.

A third class of candidate reactor devices that merit attention can be referred to as emulsion reactors, or high-shear reactors. "Emulsion" refers to a liquefied mixture that contains two distinguishable substances (or "phases") that will not mix and dissolve together readily. Most emulsions have a "continuous" phase (or matrix), which holds discontinuous droplets, bubbles, or particles of the other phase or substance. Emulsions can be highly viscous, such as slurries or pastes, and they can be foams, with tiny gas bubbles suspended in a liquid. Emulsions are widely used in foods (such as salad dressings), cosmetics (including many lotions, creams, and ointments), paints, and other products, and high-shear emulsifiers are available from companies such as IKA, which has a website (www.ikausa.com) that illustrates the internal mechanisms of various emulsifiers.

One of the challenges of methane-to-MSA conversion is the mass transfer "bottleneck" that will occur when large quantities of methane gas must be dissolved in a liquid (mainly $SO_3$ and MSA). This challenge can be met by devices that create foam-type emulsions, as disclosed and illustrated in U.S. Pat. No. 5,370,824 (Nagano et al 1994) and U.S. Pat. No. 6,471,392 (Holl and McGrevy 2002). Those systems involve two cylinders, one positioned inside the other, with an internal spinning cylinder (usually called a rotor) surrounded by a non-rotating cylinder (usually called a stator). A narrow controlled gap, in the shape of a cylindrical "annulus", is provided between the rotor and stator surfaces. If a liquid-gas mixture is pumped into this reactor, at or near one of the annulus, it will quickly form a foam, due to the high-shear mixing caused by the rapidly moving rotor surface a short distance away from the stator surface. The foaming action will create millions of tiny gas bubbles, surrounded by the viscous liquid. This creates a large gas-liquid interface area, and the large interface, combined with the shearing actions inside the foam, will cause a gas and liquid to react rapidly, as they travel through the cylinder before exiting the other end.

As taught in U.S. Pat. No. 6,471,392 (Holl and McGrevy 2002), if the cylinders are polished and smooth, and if the width of the gap between the cylinders, and the speed of rotation of the rotor, are properly controlled, a reactor can inhibit a certain type of liquid turbulence known as "Taylor vortices". Alternately, as taught in U.S. Pat. No. 5,340,891 (Imamura et al 1994), other designs can deliberately create turbulence that can promote greater mixing among some types of ingredients.

These types of emulsion reactors can be modified in ways that may increase methane-to-MSA reactions. For example, the width of the annular gap can be varied in different parts of a reactor, to provide varying levels of shearing force, and a series of gas or liquid input ports can be provided, to create sequential reaction zones.

Because of how certain dimensions and operating parameters function and interact in each of the above-listed types of reactors, it is likely that a (1) a reasonably small reactor will provide the most efficient, lowest-cost-per-ton output of MSA, and (2) the preferred way to "scale up" these types of reactors, to allow them to handle large production rates at large oil fields, will be to assemble a bank or array of numerous relatively small reactors, operating in parallel flow with each other. Each reactor in an array can operate with optimal diameters, speeds, and other parameters. Piping manifolds and metered pumps can subdivide the gas and liquid reagents into as many flow streams as desired, with each portion passing through a single relatively small reactor.

The MSA (possibly including other species) generated within the main reactor vessel 200 can be collected by any suitable means, such as condensate traps. If MSA is to be "cracked" to release methanol and $SO_2$, it will be sent to a heating vessel 300, which may contain a catalyst.

If methanol is created, it generally will be pumped into a collection or holding tank 500, for subsequent pumping into a pipeline, tanker truck or ship, nearby factory, etc. Depending on various factors (including the purity of the methane stream being processed, as well as reaction parameters inside vessels 200 and 300), other organic compounds (such as lower alkanes or derivatives, olefins or other unsaturated compounds, and aromatic compounds) may be entrained in the methanol stream. If desired, these can be separated out by, for example, a reactor bed 510 that contains a "Zeolite" (aluminosilicate) or other porous catalyst or molecular sieve material, such as "ZSM-5", sold by the ExxonMobil Corporation. The separated outputs can be sent to collection tanks 512.

Gaseous $SO_2$ also will emerge from vessel 300. It can be passed through reactor 400, which will receive oxygen from supply vessel 410 (which can use a pressure swing absorber, for concentrating oxygen from the air) to oxidize the $SO_2$ to $SO_3$. Reactor 400 can contain a catalyst to promote $SO_3$ formation. As noted above, vanadium pentaoxide is widely used commercially for this purpose, but other catalysts and reactor designs have been identified and are being evaluated, and may be preferable to $V_2O_5$. The $SO_3$ will be returned to reactor 200.

Devices, methods, and reagents to facilitate the regeneration and handling of $SO_3$ are known, including (for example):

(i) using derivatives of boron, phosphorous, or sulfur to stabilize $SO_3$ in liquid form, as described in sources such as Gilbert 1965; and, (ii) using solid supports (such as small particles in a fluidized or constrained "bed", column, or other device), to create relatively thin layers of liquid $SO_3$ that will coat the surfaces of the particles.

Any such device, method, or reagent can be evaluated to determine its suitability for use as disclosed herein.

Hydrocarbon Liquids and Olefins

Pathways are also disclosed herein for converting methane into hydrocarbons that are liquids at normal temperatures and pressures (or at relatively low pressures that can be sustained inexpensively). The discussion below focuses on gasoline, as an exemplary mixture. This is not limiting, and people skilled in hydrocarbon formulations will recognize how these teachings can be adapted to other liquids such as kerosene, naphthas, aviation fuels, diesel fuel, and fuel oils.

The term "hydrocarbon" must be addressed, since it can be used in different and potentially conflicting ways. To some chemists and chemical engineers, a "hydrocarbon" contains only hydrogen and carbon atoms, and no other atoms such as oxygen, sulfur, nitrogen, etc. (often called "hetero" atoms). To other chemists and engineers, "hydrocarbon" is more flexible, and may include some quantity of other atoms, provided that such quantities are sufficiently low that they will not seriously alter the nature or behavior of a compound or mixture.

As examples, methyl or ethyl alcohol, as pure liquids, would not be regarded as "hydrocarbons" by most chemists or engineers, since the presence of an oxygen atom in those light alcohols greatly alters their properties, compared to methane or ethane, and will turn a gas into a liquid. However, if a gasoline mixture contains 10% ethanol, it will still be regarded as gasoline, and it will still be regarded as a hydrocarbon liquid by most chemists and engineers, despite the presence of a relatively small quantity of oxygen in the mixture. Similarly, if a single oxygen atom is added to a fairly long hydrocarbon molecule that is already a liquid, the resulting molecule might still be regarded as a hydrocarbon, by at least some chemists and chemical engineers.

"Hydrocarbon" is used herein in a flexible rather than rigid manner, to include molecules and mixtures that are predominantly hydrocarbons, but which in some cases may contain relatively small quantities of oxygen or other "hetero" atoms. Although the main value of this aspect of the technology is its ability to create true hydrocarbons (with no hetero atoms) in liquid form such as gasoline, at lower costs than prior known processes that start with methane, the methods, reagents, and catalysts disclosed herein can be modified and adapted, in ways that will be recognized by those skilled in the art, to create hydrocarbon derivatives with oxygen (such as alcohols, ethers, etc.) or other heteroatoms.

The pathways herein are believed to be best suited for making relatively light and non-viscous liquids, generally having about 3 to about 8 to 10 carbon atoms. However, these methods can be adapted for making heavier molecules if desired, for fuels and/or chemical feedstocks.

It should be noted that propane and butane (with 3 and 4 carbon atoms, respectively) are liquids only under pressure; however, the pressures required are not very high, and usually range up to about 10 times atmospheric pressure, which can be sustained in relatively inexpensive tanks. Therefore, propane, butane, and LPG (liquefied petroleum gas, a mixture of mainly propane and butane) are important liquid fuels that can be made by the methods disclosed herein, and any references herein to liquids may include propane and/or butane.

It should also be noted that methyl, ethyl, propyl, and butyl alcohol are liquids that can be transported conveniently. Indeed, propyl alcohol should be regarded as a preferred fuel, for a number of reasons described below.

Processes used before the 1970's to make gasoline, diesel fuel, and other liquids from methane are described in papers posted on a website run by chemists involved in Fischer-Tropsch technology (www.fischer-tropsch.org). The Bergius process (which is no longer used commercially) used finely-divided coal, which was mixed with recycled oil and an iron catalyst, hydrogenated at high temperature and pressure to create a synthetic crude oil, which was then distilled into gasoline or aviation fuel. Fischer-Tropsch processing initially converts methane into a "synthetic gas" or "syngas" mixture of carbon monoxide and hydrogen, which is then converted, using catalysts, into heavy oils and paraffins, which are then cracked to produce lighter liguid fractions.

In addition, John Snyder and Aristid Grosse developed some relevant processes in the 1940's, described in U.S. Pat. No. 2,492,983 ("Methanol Production"), U.S. Pat. No. 2,493,038 ("Reaction of Methane with Sulfur Trioxide"), U.S. Pat. No. 2,553,576 ("Production of Organic Compounds from Methane Sulfonic Acid"), and U.S. Pat. No. 2,492,984 ("Organic Reactions", focused largely on forming liquid hydrocarbons from methanol). The Snyder and Grosse patents are more closely relevant to this invention than Bergius or Fischer-Tropsch processes; however, their work never created good yields of the desired products, and it was not commercialized.

Methanol-to-gasoline (MTG) processing changed greatly in the 1970's, when Clarence Chang and his coworkers at Mobil Oil Corporation (now Exxon-Mobil) were testing various types of Zeolite materials being developed by Mobil researchers. "Zeolite" refers to porous materials that contain silicon, aluminum, and oxygen, in crystalline lattices. The lattices have cages (cavities) connected by smaller tunnels (channels), in repeating geometric formations, and the lattice can be embedded or "doped" with catalytic atoms, ions, or molecules. Because of their structures and embedded catalysts, Zeolites and other porous catalysts can cause organic molecules to react in controllable ways.

Chang and his coworkers discovered that if methanol is passed through certain types of Zeolite, methylene groups (—CH₂—) from the methanol will begin forming chains, creating hydrocarbon liquids that can be used as gasoline. Early patents include U.S. Pat. No. 3,899,544 (Chang et al 1975), U.S. Pat. No. 4,076,761 (Chang et al 1978) and U.S. Pat. No. 4,138,442 (Chang et al 1979). Reviews include a book by Chang, *Hydrocarbons From Methanol* (Dekker, 1983), a chapter by Chang in *Methanol Production and Use* (W. Cheng & H. H. Kung, editors, Dekker, 1994), and Stöcker 1999. Stöcker 1999 provides a detailed summary, with citations to 350 articles published by other authors. It is immediately followed, in the same journal, by Keil 1999, which reviews both the historical development of MTG processing, and a number of commercial MTG installations around the world.

Related efforts also led to "methanol-to-olefin" (MTO) processing, using Zeolites that also contain phosphorus (often called "SAPO" materials, since they contain silicon, aluminum, phosphorus, and oxygen) as disclosed in U.S. Pat. No. 3,911,041 (Kaeding et al 1975). Reviews of MTO processing include Liu et al 1999, Sassi et al 2002, and Dubois et al 2003.

Figure 4:
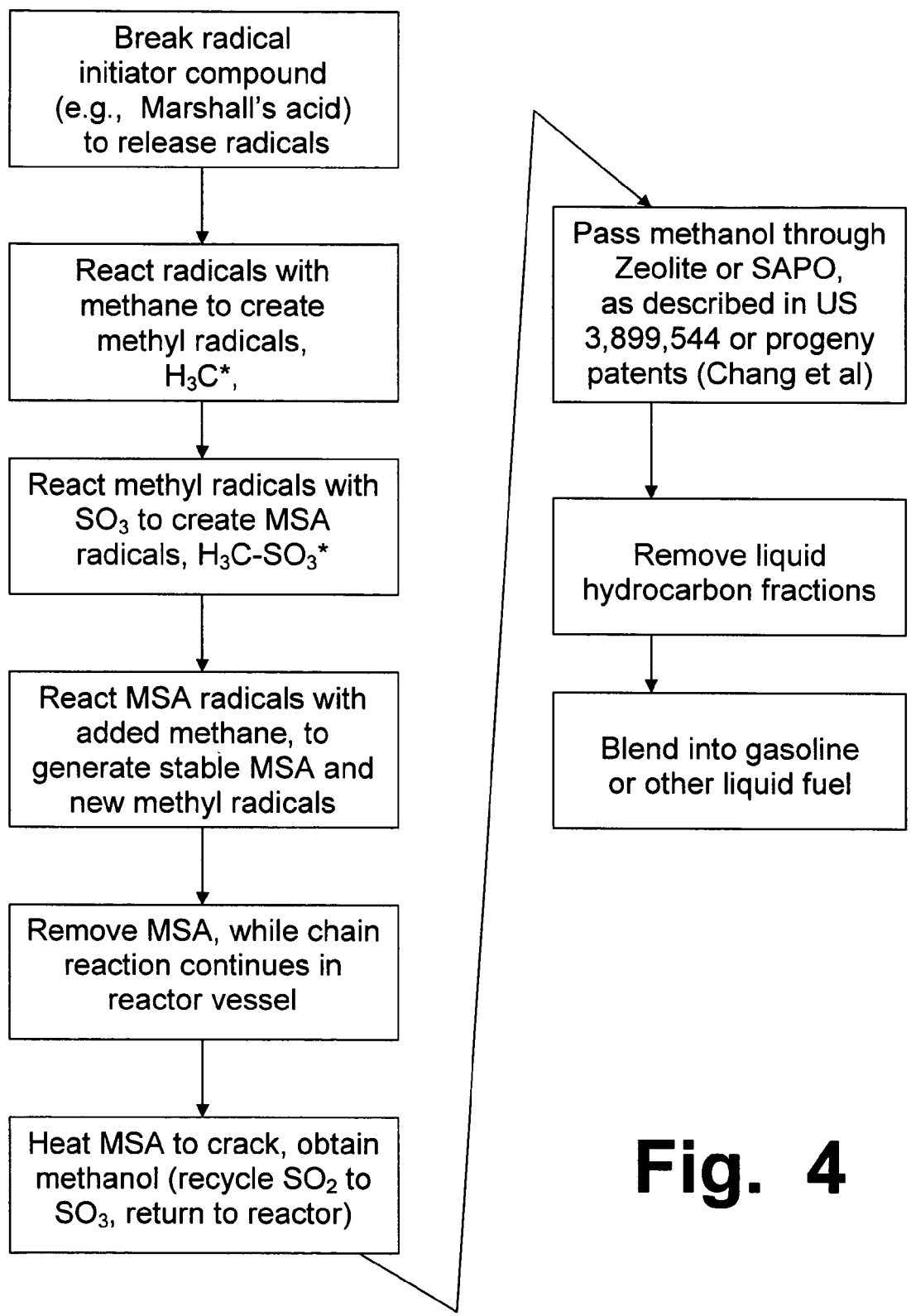
FIG. 4 is a flow chart showing steps for converting methane into liquid hydrocarbon fuel, via a pathway that cracks MSA to release methanol, which is passed through a Zeolite or other porous catalyst.

Zeolite or SAPO processing of methanol (which can be made from methane, via MSA) into gasoline or olefins is of interest herein, and is illustrated by the flow chart in FIG. 4. By combining (1) the radical-initiated MSA pathway for creating methanol, with (2) MTG or MTO processing of methanol on porous catalysts such as Zeolite or SAPO, this invention is believed to offer better methods for creating gasoline or olefins, from methane gas, than were ever known previously.

Figure 5:
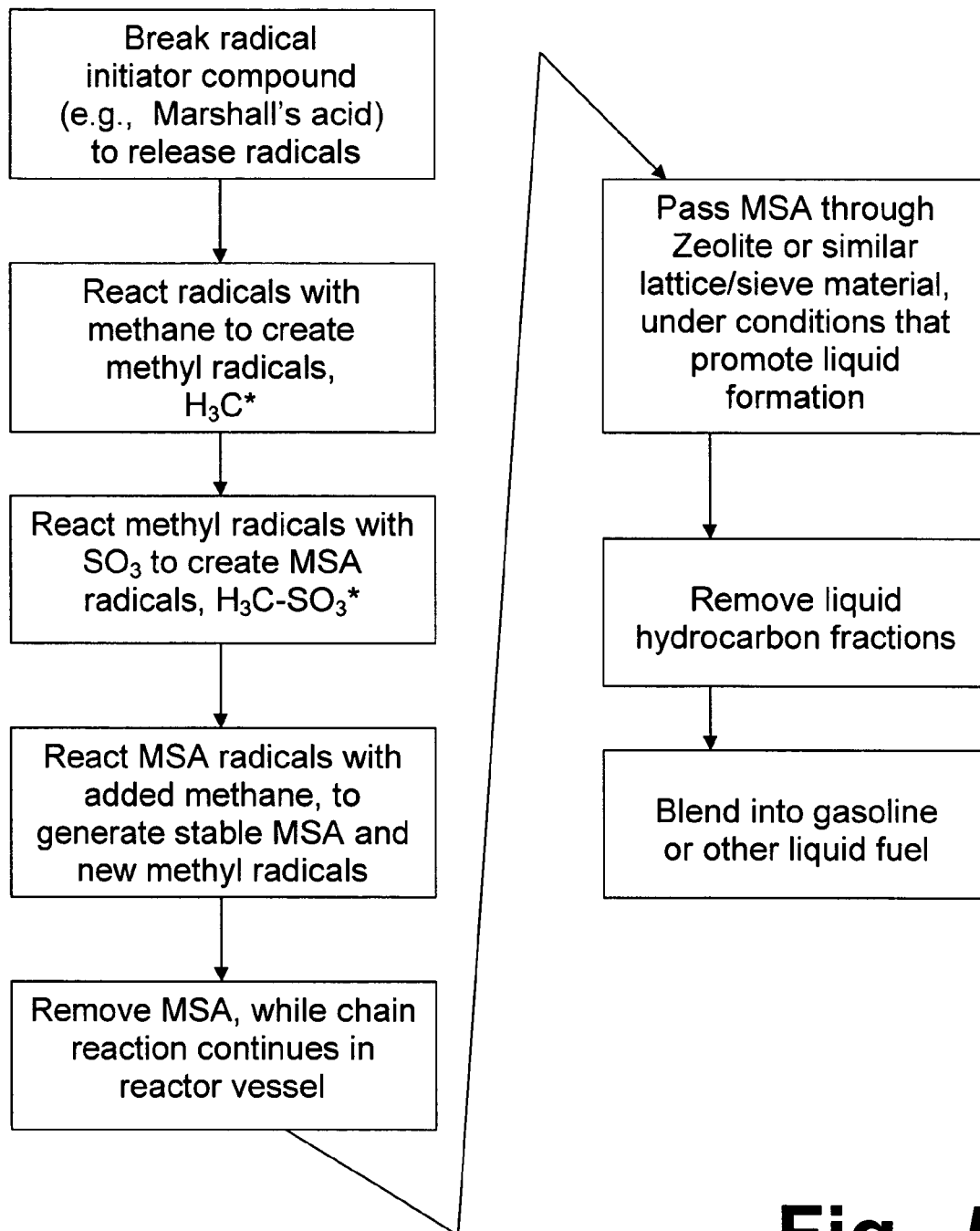
FIG. 5 is a flow chart showing steps for converting methane into liquid hydrocarbon fuel, by passing MSA directly through a porous catalyst.

However, this invention is also believed to offer even better pathways for making gasoline or olefins from methane, by directly treating MSA on Zeolite, SAPO, or similar porous catalysts, to convert the MSA directly into liquid fuels or olefins, without using methanol as an intermediate. These pathways, for MSA-to-gasoline or MSA-to-olefin processing, are shown in the flowchart in FIG. 5.

Based on computer modeling and known facts concerning electron shells and bondings of sulfur, oxygen, and carbon, it is believed that the carbon-sulfur bond in MSA can be broken more easily than the carbon-oxygen bond in methanol. Therefore, it is anticipated that porous catalysts can be identified that will provide good yields, allowing hydrocarbon fuels or olefins to be formed by passing MSA across Zeolite, SAPO, or similar catalysts that have been screened and selected for efficiency in direct processing of MSA.

The design and selection of specific Zeolite or SAPO formulations optimized for MSA processing can be done by experts who specialize in such materials. Such experts can be readily identified and located, through: (1) organizations such as The International Zeolite Association (www.iza-online.org); (2) vendor companies that sell Zeolite or SAPO materials, and that have technical specialists on their staffs or as consultants; and, (3) technical journals that publish articles in this field, such as *Microporous and Mesoporous Materials*.

Machines also have been created for rapid and automated screening of candidate porous catalysts, described in articles such as Muller et al 2003. Such devices use, for example, reactors with multiple tubes or wells, with each tube or well holding a different candidate catalyst. When a certain reagent or mixture of reagents is passed through the tubes or loaded into the wells, the product generated in each individual tube or well is collected, and delivered to an automated device such as a spectrometer or chromatograph. The tubes or wells that provide the best yields of the desired compound can be identified, and the exact content of the catalysts in the best-performing tubes or wells can be identified, studied, and used as a "baseline" or "centerpoint" in subsequent tests that use variants of the best-performing catalysts from earlier tests. Those variants can have known and controlled compositions, or "combinatorial chemistry" methods and reagents can be used to generate random or semi-random variants. Accordingly, automated systems can rapidly identify porous catalyst formulations that can promote desired reactions using known starting materials.

Any type of porous catalyst can be evaluated for potential use as disclosed herein. Such materials include, for example: (1) "monolith" materials, which contain tiny flow channels that are generally linear and parallel, passing through a silicate or other ceramic-type material; and, (2) porous materials that contain carbon atoms, such as buckyballs or nanotubes, as described in U.S. Pat. No. 6,656,339 (Talin et al 2003) and numerous other patents. Voltage-assisted reactions (as described in U.S. Pat. Nos. 6,214,195 and 6,267,864 (Yadav et al 2001)) also can be evaluated for this type of processing.

After experts who specialize in porous catalysts have seen the disclosures herein, they will be able to identify catalyst formulations that can convert MSA into liquid hydrocarbon, liquid oxygenates, and/or liquid olefins, in commercial quantities. Therefore, the disclosures herein will enable the development of better methods for converting methane gas into liquid hydrocarbons, oxygenates, and olefins than have previously been available, by passing MSA directly through or across porous catalysts, without having to go through methanol as an intermediate.

Accordingly, FIG. 6 depicts a stepwise condensation of MSA using a Zeolite, SAPO, or other porous catalyst, under conditions that enable molecules of MSA to contribute methylene groups to a growing hydrocarbon chain. This drawing presumes that the conditions and chosen catalyst will initially cause an ethene molecule to form, to provide what will become a "condensation nucleus" for subsequent lengthening of the chain (alternately, the catalyst can be "seeded" with ethene, to help the chain formation get started). Because of certain electron-related factors, it is believed that subsequently additional MSA molecules will most likely insert their methylene groups into the electron-rich site provided by the double bond, in a manner that effectively (1) pushes out the #2 carbon atom in the double bond, so that it joins the growing chain, (2) replaces the old #2 carbon atom with a new #2 carbon atom, and (3) forms a new double bond, which will provide a good site of insertion for the next MSA molecule to insert another methylene group, thereby leading to mixtures that will contain enriched quantities of alpha olefins.

The stepwise condensation of longer hydrocarbon chains into liquids can be terminated as soon as the chains reach a desired length. (which will depend on economic and market factors at any particular site). This offers a major advantage over Fischer-Tropsch processing, which "overshoots" the gasoline range and creates thick and heavy oils and paraffins, which then must be distilled and/or cracked (at additional cost) to reduce them to desired lengths.

Other Classes of Chemicals

The methods disclosed herein for processing methane into other compounds can be expanded, adapted, and otherwise developed into methods for manufacturing other organic compounds, using the pathways described below and illustrated in the named figures, or using alternate pathways that will be apparent to those skilled in the art after they have seen the disclosures herein. The following subsections offer a number of examples.

Alkylamines

The synthesis of three progressively larger methylamines (mono-methylamine, di-methylarnine, and tri-methylamine) can also be accomplished using MSA as a reagent. All of these share a straightforward reaction pathway, which initially results in the synthesis of mono-methyl-amine (usually referred to simply as methylamine) . MSA, synthesized as described above and illustrated in FIG. 2, is reacted with ammonia - - - (either in its $NH_3$ form, or in its ionic form, $NH_4^+$) at temperature and pressure combinations such as described in articles such as Mochida et al 1983 and Sagawa et al 1991. Methyl groups from MSA can displace one or more of the hydrogen atoms in ammonia. If one methyl group displaces a single hydrogen atom on ammonia, the product will be (mono-)methylamine; if two methyl groups from MSA displace two hydrogen atoms on ammonia, di-methylamine will be formed, etc.

When MSA donates its methyl group to ammonia, the "leaving group" will be $SO_3H$, in radical or ionic form (for convenience, any group with at least one sulfur atom and at least one oxygen atom is referred to as a sulfate group, regardless of what its oxidation state may be; this includes sulfite groups, and it applies regardless of whether a sulfate group is in a radical, ionic, pendant moiety, or other form). The sulfate radical or ion that leaves MSA will establish an acidic equilibrium with hydrogen ions in solution (including hydrogen atoms that have been displaced from the ammonia, as well as hydrogen atoms that have spontaneously dissociated from molecules of MSA. This generates sulfurous acid, $H_2SO_3$, which can be removed from the reactor by condensation or adsorption. Sulfurous acid can be thermally cracked at high temperature ("thermolysis"), to release $SO_2$ and water. The $SO_2$ can be oxidized to $SO_3$ and recycled back - - - - into the reactor that is converting methane into MSA, to prevent or minimize waste.

If a limited quantity of MSA is added to a surplus of ammonia, the predominant product will be mono-methylamine. This product can be separated from ammonia by distillation, allowing unreacted ammonia to be recycled through the reactor. If a mixture of mono-methylamine, di-methylamine, and tri-methylamine is created, they can be separated from each other by distillation or other processing. Accordingly, any ratio of MSA to ammonia can be tested, and used if found to be economically preferable for a particular operation. Various stoichiometric ratios of MSA to ammonia can be tested to determine which will provide the preferred yields at any particular location, which will depend on economic and market factors.

Aromatic Compounds

Various aromatic compounds can be methylated, using MSA as a methyl donor. One example involves the conversion of toluene (with a single methyl group attached to a benzene ring) into para-xylene (two methyl groups attached to opposite ends of a benzene ring). If desired, para-xylene can be oxidized into a compound called terephthalic acid (TPA), which has two carboxylic acid groups at opposite ends of the benzene ring. TPA is useful as a monomer in the plastics industry.

If a second MSA treatment step is used, TPA can be converted into dimethyl-terephthalate (DMT), another valuable monomer used in the plastics industry.

Unsaturated Compounds

In addition to being able to create olefins, MSA also can be used to add methyl or methylene groups to various unsaturated compounds. For example, MSA can convert methacrylic acid into methyl-methacrylate, a compound used to make plastics and polymers. A methyl group from MSA will displace the hydrogen on the hydroxy group of methacrylic acid, creating a pendant methyl group that is attached to a carbon atom through an ester linkage, which is useful in various reactions and products. This type of methylation is described in reports such as Porcelli et al 1986. Chemists will recognize other pathways that can use MSA at one or more steps of a reaction pathway, to create other valuable compounds.

Dimethyl Ether

Dimethyl ether (DME, $H_3COCH_3$) has two methyl groups, with an oxygen atom between them. It can be prepared from MSA in any of several ways. If MSA is cracked to release methanol, the methanol can be converted to DME by a dehydrating agent such as zinc chloride (e.g., U.S. Pat. No. 2,492,984, Grosse & Snyder 1950), or by passing the methanol through a suitable Zeolite (e.g., U.S. Pat. No. 3,036,134, Mattox 1962). Alternately, MSA may be converted into DME by direct processing, to avoid a methanol intermediate. This assertion is supported by comments in U.S. Pat. No. 4,373,109 (Olah 1983), Olah 1987, and Zhou et al 2003, which describe products formed by substituted alkanes passed through Zeolites containing certain metal oxides. It is believed that MSA can be induced to behave in ways comparable to other substituted methyl compounds having electronegative atoms bonded to carbon, which have shown repeatedly that they can be split apart by Zeolites.

Formation of DME may require addition of oxygen to a Zeolite. If necessary, it can be accomplished by pumping ozone, oxygen gas, air, nitrous or nitric or other inorganic oxides, or other oxygen donor compounds into the porous lattice.

Formaldehyde

Various pathways can be used to convert MSA or methanol into formaldehyde. For example, methanol formed from MSA can be converted by iron-molybdenum, silver, vanadium, or other catalysts described in Lefferts et al 1986, Hara et al 1996, and Tatibouet 1966 and 1996. Alternately, if MSA is converted into DME, the DME can be converted into formaldehyde using bismuth, molybdenum, or iron catalysts, as described in U.S. Pat. Nos. 4,439,624 and 4,442,307 (Lewis et al 1984) or Liu and Iglesia 2002.

EXAMPLES

Example 1

Equipment and Reagents

The initial confirmatory tests, described in Examples 1-6, were done in the laboratories of Prof. Ayusman Sen, in the Chemistry Department at Pennsylvania State University. Experiments were carried out under inert gas (nitrogen, $N_2$) in a glovebox or glovebag. Except as noted below, the reactions were carried out in a sealed vessel designed to withstand high pressures (commonly referred to in chemistry labs as "bombs"), containing a glass liner (this liner, which can be easily removed for cleaning and sterilization, will not break when high pressures are reached inside the bomb, because pressures are equal on both sides of the walls of a liner). The bomb used has ⅜ inch stainless steel walls, and an internal chamber 1.5 inches in diameter and 4.5 inches high. The glass liner had an internal diameter of 1.24 inches, a height of 4 inches, and a wall thickness of 1/16 inch. A 1-inch stirring bar was used in some tests.

In a number of experiments, a vial was placed inside the liner, to prevent any direct mixing of a first liquid in the bottom of the liner, and a second liquid in the vial. The vial had a 1-inch outside diameter, a wall thickness of 1/16 inch, and a height of 2.25 inches. The diameter of the vial opening (with threads to accommodate a screw cap) was 5/8 inch. A 1/2 inch stirring bar was used in some tests.

Example 2

Preparation of Marshall's Acid

To prepare Marshall's acid, gaseous $SO_3$ in $N_2$ was loaded into a vessel containing 70% $H_2O_2$ in water, at 13 to 15° C. The reaction continued with stirring until essentially all liquid reagents had been consumed, confirmed by presence of a consistent viscous solution with solid crystals and no inhomogeneous liquids.

In Run #1, 6.9 g (86.3 mmol) of $SO_3$ was absorbed in 1.1 g of 70% $H_2O_2$ (22.7 mmol) in water (17.7 mmol), for 5.5 hours. After accounting for the diversion of some $SO_3$ into $H_2SO_4$, the molar ratio of $SO_3$ to $H_2O_2$ was 3:1. It was presumed that all $H_2O_2$ was converted to Marshall's acid ($H_2S_2O_8$), and all water was converted to $H_2SO_4$. Calculations and assumptions indicated Marshall's acid at 22.7 mmol (56.2% of the total solution, by weight), and sulfuric acid at 17.7 mmol (21.3%), with unreacted $SO_3$ present at 23.2 mmol (22.5%).

In Run 2, 5.2 g (65 mmol) of $SO_3$ was absorbed in 1.2 g of 70% $H_2O_2$ (25 mmol) in water (19.4 mmol), for 5.5 hours. Calculations and assumptions as described above indicated Marshall's acid at 20.6 mmol (62.5%), sulfuric acid at 19.4 mmol (29.7%), and Caro's acid at 4.4 mmol (7.8%).

In Run 3, 8.3 g (103.8 mmol) of $SO_3$ was absorbed in 1.8 g of 70% $H_2O_2$ (37.0 mmol) in water (30.0 mmol), for 7 hours. Calculations and assumptions indicated Marshall's acid at 37.0 mmol (71.3%), and sulfuric acid at 30 mmol (28.7%).

In Run 4, 8.3 g (103.8 mmol) of $SO_3$ was absorbed in 2.1 g of 70% $H_2O_2$ (43.2 mmol) in water (35.0 mmol), for 7 hours. Calculations and assumptions indicated Marshall's acid at 25.6 mmol (47.7%), sulfuric acid at 35 mmol (33%), and Caro's acid at 17.6 mmol (19.2%).

Example 3

Procedures for Testing MSA Formation

The tests described below used MSA/$SO_3$ mixtures as the liquid media (gaseous $SO_3$ can be absorbed in MSA at ratios up to about 10:1). A solution of $SO_3$, dissolved in a known quantity of liquid MSA that acted as an amphoteric solvent, was placed in a glass vial, described above. 1 to 2 grams of Marshall's acid solution (Example 2) was placed in the same vial. The vial was placed in the larger glass liner inside the bomb, and 3 to 5 g of stabilized liquid $SO_3$ was loaded into the liner. This approach (dividing the $SO_3$ into two separate zones) was taken to prevent the Marshall's acid from being overloaded with $SO_3$, since high concentrations of $SO_3$ can degrade Marshall's acid, releasing oxygen and destroying its peroxide bond.

The bomb was sealed and pressurized with 800-1400 psi of methane. It was heated to 48-52° C., and pressure was monitored. Heating was continued until the pressure dropped to an asymptotic level. The bomb was allowed to cool gradually to room temperature, pressure was released slowly, the bomb was opened, and the solution in the vial was diluted with 5-10 mL of water. The liquid was then analyzed, via $^1H$ nuclear magnetic resonance (NMR).

In most cases, MSA was the only product found in the liquid phase, as indicated by NMR. It was quantified, using integration of peak intensity compared to a dimethyl sulfoxide standard in a capillary tube, to confirm that additional MSA had indeed been formed, in addition to the solvent MSA in the liquid that was initially loaded into the vial.

The gas mixture in the cooled bomb was analyzed by gas chromatography. No $CO_2$ was detected in any runs.

Example 4

First Run: Methane Yield 40.4%, $SO_3$ Yield 96.0%

In the first reaction test, 1.0 gram of Marshall's acid preparation (Marshall's acid 56.2%, sulfuric acid 21.3%, $SO_3$ 22.5%) was added to 50 mmol of MSA and 63 mmol of $SO_3$. 2.8 g (35 mmol) of stabilized liquid $SO_3$ was added to the liner, outside the vial. The bomb was pressurized to 800 psi with methane, and heated at 48-52° C.

70 psi of pressure drop was observed within 2 hours, and the vessel was recharged with 50 additional psi of methane. The total pressure drop was 120 psi over the next 2 hours (i.e., after 4 hours total), and the vessel was recharged with an additional 50 psi of methane. Total pressure drop was 250 psi over 14 hours.

Total methane injected into the bomb was measured and calculated at 240 mmol, and total $SO_3$ in the liquid media (i.e., dissolved in MSA and placed inside the vial) was 101 mmol. Yield of newly-formed MSA was measured and calculated as 97 mmol (147 mmol total, minus 50 mmol already present in the MSA/$SO_3$ liquid media). This indicated a methane conversion yield of 40.4%, and an $SO_3$ conversion yield of 96.0%.

Example 5

Subsequent Runs: Methane Yields 33 to 43%, $SO_3$ Yields 92 to 99%

In runs 2, 3, and 4, carried out in essentially the same manner as run 1 with slightly varying quantities of Marshall's acid solution from the preparations described above and varying quantities (pressures) of methane and $SO_3$, methane conversion yields were determined to be 40.6%, 43.3%, and 33.6%, and $SO_3$ conversion yields were determined to be 99.1%, 92.6%, and 92.6%, respectively.

Examination and comparison of the data indicated that concentration of methane in the bomb was the rate determining factor, since increasing methane pressure increased the rate of the reaction. It also appeared that the key step for increasing the rate of the reaction would involve increasing the solubility of $CH_4$ in a liquid phase.

In addition, various calculations (including a calculated rate constant of $3.0 \times 10^{-5}$ per second, for homolysis of Marshall's acid in $SO_3$ at 50° C.) indicated that the rate of conversion of methane to MSA was about 20 times faster than the rate of homolysis of Marshall's acid. This helped explain why the pressure continued to drop over spans of 10 hours (in the laboratory test conditions that were used), and why conversion of $SO_3$ was very high, up to 99%. The data indicated that if the process is scaled up to industrial levels, with continuous-flow reactors designed for high throughputs rather than small-volume batch reactors, efficient reaction levels could be achieved in minutes or even seconds, rather than over a span of hours.

Example 6

No Conversion by Potassium Salt of Marshall's Acid

As a comparative experiment, 270 mg of the potassium salt of Marshall's acid ($K_2S_2O_8$; 1.0 mmol) was loaded into the vial, and 13.5 g of stabilized $SO_3$ was loaded into the liner, using procedures identical to the testing of the free acid form of Marshall's acid, as disclosed above. The bomb was pressurized with 800 psi of methane, and heated at 48-52° C. for 20 hours. However, no pressure drop was observed. The temperature was increased to 75-80° C. for an additional 16 hours, but still no pressure drop was observed. The absence of any pressure drop indicates that the potassium salt of Marshall's acid failed to initiate any reaction between the methane, and the $SO_3$.

Example 7

Subsequent Tests in Larger Batch Reactor

After the initial confirmatory tests described above had been completed at Penn State University, subsequent tests were carried out at SLI Technologies, Inc., in Milton, Fla., using comparable but larger equipment. The product was analyzed by an outside laboratory, and the organic phase was found to consist of at least 99.5% pure MSA.

Thus, there has been shown and described new and improved methods, devices, reagents, and catalysts means for creating methanol and other derivatives, intermediates, and products from methane gas. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Basickes, N., et al, *J Am Chem Soc* 118: 13111 (1996)
Blavins, J. J., et al, *J Org Chem* 66: 4285 (2001)
Broekhuis, R. R., et al, *Catalysts Today* 69: 887 (2001)
Chuang, T. J., et al, *J Electron Spectroscopy & Related Phenomena* 98-99: 149 (1999)
Danon, A., et al, *Rev Sci Instrum* 58: 1724 (1987)
Dubois, D. R., et al, *Fuel Proc. Technology* 83: 203 (2003)
Dunn, J. P., et al, *Applied Catalysis B:* Environmental 19: 103 (1998)
Gesser, H. D., et al, *Chem Rev* 85: 235 (1985)
Giakoumelou, I., et al, *Catalysis Letters* 78: 209 (2002)
Gilbert, G. E., *Sulfonation and Related Reactions* (Interscience Publishers, 1965)
Gilson, T. R., *J Solid State Chemistry* 117: 136 (1995)
Hayes, R. E., et al, *Introduction to Catalytic Combustion* (Gordon & Breach Science Publ., Amsterdam, 1997)
Keil, F. J., *Microporous and Mesoporous Materials* 29: 49 (1999)
Lefferts, L., et al, *Applied Catalysis* 23: 385 (1986)
Li, P., et al, *Surface Science* 380: 530 (1997)
Li, A-H,. et al, *Chem Rev* 97: 2341 (1997)
Lie, L. H., et al, *J Phys Chem B* 106: 113 (2002)
Liu, W., *AIChE Journal* 48: 1519 (2002)
Liu, W., et al, *Ind Eng Chem Res* 41: (2002)
Liu, Z. and Liang, J., *Current Opinion in Solid State and Materials Science* 4: 80 (1999)
Liu, H., et al, *J Catalysis* 208: 1 (2002)
Lobree, L. J., et al, *Ind Eng Chem Res* 40: 736 (2001)
Mukhopadhyay, S., et al, *Angew Chem Int Ed* 42: 2990 (2003)
Mukhopadhyay, S., et al, *Amer Chem Soc* 2002: A-E (2002)
Muller, A., et al, *Catalysis Today* 81: 337 (2003)
Olah, G. A., *Acc Chem Res* 20: 422 (1987)
Peng, X-D., et al, *Rev Sci Instrum* 63: 3930 (1992)
Periana, R. A., et al, *Science* 259: 340 (1993)
Periana, R. A., et al, *Chem Commun* 2002: 2376 (2002)
Periana, R. A., et al, *Science* 280: 560 (1998)
Porcelli, R. V., et al, *Hydrocarbon Proc.*, March 1986: 37 (1986)
Raja, L. L., et al, *Catalysis Today* 59: 47 (2000)
Romm, L., et al, *J Phys Chem A* 105: 7025 (2001)
Sagawa, K., et al, *J Catalysis* 131: 482 (1991)
Sassi, A., *J Phys Chem B* 106: 8768 (2002)
Stöcker, M., *Microporous Mesoporous Materials* 29: 3 (1999)
Tatibouet, J. M., et al, *J Catalysis* 161: 873 (1966)
Tatibouet, J. M., et al, *Applied Catalysis* 148: 213 (1996)
te Velde, G., et al, *J Comput Chem* 22: 931 (2001)
Won, T-J., et al, *Inorganic Chemistry* 34: 4499 (1995)
Zhai, R—S., et al, preprint downloaded from American Chemical Society website (Langmuir),
Zhou, X., et al, *Chem Commun:* 2294 (2003)

The invention claimed is:

1. A method for converting methane into methanesulfonic acid comprising the steps of:
   a. removing hydrogen atoms from methane, thereby generating methyl radicals, each having an unpaired electron;
   b. contacting the methyl radicals with sulfur trioxide, under conditions that enable the methyl radicals to react with the sulfur trioxide to form methylated oxide radicals having sufficient reactivity to remove hydrogen atoms from methane; and,
   c. reacting the methylated oxide radicals with methane, under conditions that enable the methylated oxide radicals to remove hydrogen atoms from the methane, thereby forming methanesulfonic acid and additional methyl radicals,
   wherein steps (b) and (c) are carried out under essentially anhydrous conditions, using methanesulfonic acid as a solvent,
   and wherein the method uses at least one radical-initiator compound that does not contain any metallic or mineral ion or salt.

2. The method of claim 1 wherein a series of reaction steps is initiated by treating methane with at least one radical initiator compound to create the methyl radicals, and then sustained by adding additional quantities of sulfur trioxide and methane to at least one reactor device containing the methylated oxide radicals.

3. The method of claim 1, wherein the methylated oxide radicals comprise methanesulfonic acid radicals.

4. The method of claim 1, wherein at least a portion of the methanesulfonic acid is converted into dimethyl ether.

5. The method of claim 4, wherein at least a portion of the methanesulfonic acid is treated to release sulfur dioxide.

6. The method of claim 5, wherein at least a portion of the sulfur dioxide is oxidized to convert it into sulfur trioxide, and at least a portion of said sulfur trioxide is recycled into a reactor vessel that contains methyl radicals.

7. The method of claim 1 wherein the series of reaction steps, taken together, generate non-recyclable byproducts in a total quantity of less than 10 percent, by weight, of methanesulfonic acid formed by the method.

8. The method of claim 1, wherein, in step (a), hydrogen atoms are initially removed from methane by means that comprise contacting methane with a radical-initiator compound that has been converted into at least one unstable intermediate having an unpaired electron.

9. The method of claim 8, wherein the unstable intermediate is formed from a peroxide compound.

10. The method of claim 8, wherein the radical-initiator compound comprises a symmetric inorganic di-acid compound having a peroxide linkage, and wherein said symmetric inorganic di-acid compound will generate two identical oxygen radicals if the peroxide linkage is broken.

11. The method of claim 10, wherein the symmetric inorganic di-acid is selected from the group consisting of peroxy-disulfuric acid and peroxy-diphosphoric acid.

12. A process for converting methane into a methylated oxide compound, said process comprising the steps of:
 (i) reacting a methyl radical with an oxide compound selected from the group consisting of sulfur, nitrogen, and phosphorous oxides to create a methylated oxide radical;
 (ii) reacting the methylated oxide radical with methane, creating a reaction mixture that contains methane, methyl radicals, said oxide compound, and a methylated oxide compound containing an element selected from the group consisting of sulfur, nitrogen and phosphorous; and,
 (iii) removing a portion of the methylated oxide compound from the reaction mixture,
 wherein the process is carried out under essentially anhydrous conditions, using a portion of said methylated oxide compound as a solvent,
 and wherein the method uses at least one radical-initiator compound that does not contain any metallic or mineral ion or salt.

13. The process of claim 12, wherein said process is carried out within a reactor vessel that allows continuous addition of methane and said selected oxide compound to said reaction mixture, and continuous removal of said methylated oxide from the reactor vessel.

14. The process of claim 12, wherein the selected oxide compound comprises sulfur trioxide.

15. The process of claim 12, wherein the methylated oxide radicals comprise methylsulfonic acid radicals.

16. The process of claim 12, wherein all reactions are carried out using essentially anhydrous conditions.

17. The process of claim 12, wherein the series of reaction steps, taken together, generate non-recyclable byproducts in a total quantity of less than 10 percent, by weight, of stabilized methylated oxide molecules that are removed by the process.

18. A method for converting methane into methanesulfonic acid comprising the steps of:
 a. removing hydrogen atoms from methane, thereby generating methyl radicals, each having an unpaired electron;
 b. contacting the methyl radicals with sulfur trioxide, under conditions that enable the methyl radicals to react with the sulfur trioxide to form methylated oxide radicals having sufficient reactivity to remove hydrogen atoms from methane; and,
 c. reacting the methylated oxide radicals with methane, under conditions that enable the methylated oxide radicals to remove hydrogen atoms from the methane, thereby forming methanesulfonic acid and additional methyl radicals,
 wherein steps (b) and (c) are carried Out under essentially anhydrous conditions, using methanesulfonic acid as a solvent,
 and wherein the method does not introduce metallic or mineral ions or salts into a reaction solution containing sulfur trioxide and methanesulfonic acid.

19. The method of claim 18 wherein a series of reaction steps is initiated by treating methane with at least one radical initiator compound to create the methyl radicals, and then sustained by adding additional quantities of sulfur trioxide and methane to at least one reactor device containing the methylated oxide radicals.

20. The method of claim 18, wherein at least a portion of the methanesulfonic acid is converted into dimethyl ether.

21. The method of claim 20, wherein at least a portion of the methanesulfonic acid is treated to release sulfur dioxide.

22. A process for converting methane into a methylated oxide compound, said process comprising the steps of:
 (i) reacting a methyl radical with an oxide compound selected from the group consisting of sulfur, nitrogen, and phosphorous oxides to create a methylated oxide radical;
 (ii) reacting the methylated oxide radical with methane, creating a reaction mixture that contains methane, methyl radicals, said oxide compound, and a methylated oxide compound containing an element selected from the group consisting of sulfur, nitrogen and phosphorous; and,
 (iii) removing a portion of said methylated oxide compound from the reaction mixture,
 wherein the process is carried out under essentially anhydrous conditions, using a portion of said methylated oxide compound as a solvent,
 and wherein the method does not introduce metallic or mineral ions or salts into a reaction solution containing said methylated oxide compound.

23. The process of claim 22, wherein said process is carried out within a reactor vessel that allows continuous addition of methane and said selected oxide compound to said reaction mixture, and continuous removal of said methylated oxide from the reactor vessel.

24. A method for converting methane into methanesulfonic acid comprising the steps of:
 a. removing hydrogen atoms from methane, thereby generating methyl radicals, each having an unpaired electron;
 b. contacting the methyl radicals with sulfur trioxide, under conditions that enable the methyl radicals to react with the sulfur trioxide to form methylated oxide radicals having sufficient reactivity to remove hydrogen atoms from methane; and,
 c. reacting the methylated oxide radicals with methane, under conditions that enable the methylated oxide radicals to remove hydrogen atoms from the methane, thereby forming methanesulfonic acid and additional methyl radicals,
 wherein steps (b) and (c) are carried out under essentially anhydrous conditions,
 and wherein the method uses methanesulfonic acid as a solvent in step (b) to increase solubility of methane gas in a liquid reaction mixture containing sulfur trioxide.

25. The method of claim 24, wherein a series of reaction steps is initiated by treating methane with at least one radical initiator compound to create the methyl radicals, and then sustained by adding additional quantities of sulfur trioxide and methane to at least one reactor device containing the methylated oxide radicals.

26. The method of claim 24, wherein at least a portion of the methanesulfonic acid is converted into dimethyl ether.

27. The method of claim 24, wherein at least a portion of the methanesulfonic acid is treated to release sulfur dioxide.

* * * * *